US009028809B2

(12) United States Patent
Stinchcomb et al.

(10) Patent No.: US 9,028,809 B2
(45) Date of Patent: May 12, 2015

(54) COMPOSITIONS, METHODS AND USES FOR EXPRESSION OF ENTEROBACTERIUM-ASSOCIATED PEPTIDES

(75) Inventors: Dan T. Stinchcomb, Fort Collins, CO (US); Jorge E. Osorio, Mount Horeb, WI (US); Timothy D. Powell, Fort Collins, CO (US); Joseph N. Brewoo, Madison, WI (US)

(73) Assignee: Takeda Vaccines, Inc., Deerfield, IL (US)

( * ) Notice: Subject to any disclaimer, the term of this patent is extended or adjusted under 35 U.S.C. 154(b) by 0 days.

(21) Appl. No.: 13/511,652

(22) PCT Filed: Nov. 24, 2010

(86) PCT No.: PCT/US2010/058094
§ 371 (c)(1),
(2), (4) Date: Oct. 19, 2012

(87) PCT Pub. No.: WO2011/066454
PCT Pub. Date: Jun. 3, 2011

(65) Prior Publication Data
US 2013/0034583 A1 Feb. 7, 2013

Related U.S. Application Data

(60) Provisional application No. 61/264,144, filed on Nov. 24, 2009.

(51) Int. Cl.
*A01N 63/00* (2006.01)
*A61K 39/275* (2006.01)
*A61K 39/00* (2006.01)
*A61K 39/02* (2006.01)

(52) U.S. Cl.
CPC ........... *A61K 39/025* (2013.01); *A61K 39/0291* (2013.01); *A61K 2039/5256* (2013.01); *C12N 2710/24134* (2013.01); *C12N 2710/24141* (2013.01)

(58) Field of Classification Search
None
See application file for complete search history.

(56) References Cited

U.S. PATENT DOCUMENTS

| 6,468,982 | B1 | 10/2002 | Weiner et al. | |
| 2003/0095987 | A1 | 5/2003 | Haller et al. | |
| 2009/0047293 | A1* | 2/2009 | Grandi et al. | 424/164.1 |
| 2010/0129404 | A1* | 5/2010 | Hochrein et al. | 424/232.1 |
| 2012/0328653 | A1* | 12/2012 | Pantaleo et al. | 424/206.1 |

FOREIGN PATENT DOCUMENTS

WO 200979564 A2 6/2009

OTHER PUBLICATIONS

Osorio et al. Vaccine 21: 1232-1238, 2003.*
Ramirez et al. J. Virol. 74: 923-933, 2000.*
Rocke et al., Further development of raccoon poxvirus-vectored vaccines against plague (*Yersinia pestis*). Vaccine ePub Oct. 29, 2009, 28:338-344.
International Search Report and Written Opinion, PCT/US10/58094, Mar. 10, 2011.
Drexler et al., Modified vaccinia virus Ankara as antigen delivery system: how can we best use its potential? Current Opinion in Biotechnology, 2004, vol. 15, No. 6, pp. 506-512.
Rocke et al., Immunization of black-tailed prairie dog against plague through consumption of vaccine-laden baits. Journal of Wildlife Diseases, 2008, vol. 44, No. 4, pp. 930-937.
Mencher et al., Protection of Black-Tailed Prairie Dogs (*Cynomys ludovicianus*) against Pague after Voluntary Consumption of Baits Containing Recombinant Raccoon Poxvirus Vaccine. Infection and Immunity, 2004, vol. 72, No. 9, pp. 5502-5505.
Rocke et al., Limited infection upon human exposure to a recombinant raccoon pox vaccine vector. Vaccine, 2004, vol. 22, No. 21-22, pp. 2757-2760.

* cited by examiner

*Primary Examiner* — S. Devi
(74) *Attorney, Agent, or Firm* — Faegre Baker Daniels LLP

(57) ABSTRACT

Embodiments of the present invention generally disclose methods, compositions and uses for generating and expressing enterobacterial-associated peptides. In some embodiments, enterobacterial-associated peptides include, but are not limited to plague-associated peptides. In certain embodiments, methods generally relate to making and using compositions of constructs including, but not limited to, attenuated or modified vaccinia virus vectors expressing enterobacterial-associated peptides. In other embodiments, vaccine compositions are reported of use in a subject.

9 Claims, 10 Drawing Sheets

Fig. 5

Table 3: Vectors using MVA transfer vector backbones.

| Vector designation | cloning vector | Promoter | | IRES | | Secretory signal | | | | Expressed antigen(s) | | | |
|---|---|---|---|---|---|---|---|---|---|---|---|---|---|
| | | H6 | Se/I | IRES (A6) | IRES (A7) | tPA | C13L | B8R | F1 | LcrV | LcrVt | YopD | YscF |
| pDIIIgfp | X | X | | | | | | | | | | | |
| pI1 | X | X | | | | | | | | | | | |
| pI2 | X | | X | | | | | | | | | | |
| pI3 | X | X | | X | | X | | | | | | | |
| pI4 | X | | X | X | | X | | | | | | | |
| pI41 | X | | X | X | | | X | | | | | | |
| pI42 | X | | X | X | | | | X | | | | | |
| pI43 | X | | X | | | X | | | | | | | |
| pI44 | X | | X | | | | X | | | | | | |
| pI45 | X | | X | | | | | X | | | | | |
| pI5 | | X | | | X | X | | | X | | | | |
| pI6 | | | X | | X | X | | | X | | | | |
| pI9 | | X | | X | | X | | | X | | | | |
| pI10 | | | X | X | | X | | | X | | | | |
| pI11 | | X | | | | | | | X | | | | |
| pI12 | | | X | | | | | | X | | | | |
| pI33 | | | | X | | X | | | X | | | | |
| pI34 | | | | | | | | | X | | | | |
| pI46 | | | X | X | | | X | | X | | | | |
| pI47 | | | X | X | | | | X | X | | | | |
| pI48 | | | X | | | X | | | X | | | | |
| pI49 | | | X | | | | X | | X | | | | |
| pI50 | | | X | | | | | X | X | | | | |
| pI7 | | X | | X | | X | | | | X | | | |
| pI8 | | | X | X | | X | | | | X | | | |
| pI25 | | X | | | | | | | | X | | | |
| pI26 | | | X | | | | | | | X | | | |
| pI39 | | | X | | | | | | | | X | | |
| pI40 | | | X | X | | X | | | | | X | | |
| pI13 | | X | | | | | | | | | | X | |
| pI14 | | | X | | | | | | | | | X | |
| pI27 | | | X | X | | X | | | | | | X | |
| pI28 | | | X | X | | X | | | | | | X | |
| pI21 | | X | | | | | | | | | | | X |
| pI22 | | | X | | | | | | | | | | X |
| pI31 | | X | | X | | X | | | | | | | X |
| pI32 | | | X | X | | X | | | | | | | X |

Fig. 7

```
SEQUENCE LISTING

<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: Yersinia pestis antigen primer

<400> SEQUENCE: 1
gtgagtcgac atgaaaaaaa tcagttccgt tatc                              34

<210> SEQ ID NO 2
<211> LENGTH: 32
<212> TYPE: DNA
<213> ORGANISM: Artificial Sequence
<220> FEATURE:
<223> OTHER INFORMATION: Yersinia pestis antigen primer

<400> SEQUENCE: 2
gcgaattctt attggttaga tacggttacg gt                                32

<210> SEQ ID NO 3
<211> LENGTH: 35
<212> TYPE: DNA
<213> ORGANISM: Artificial Sequence
<220> FEATURE:
<223> OTHER INFORMATION: Yersinia pestis antigen primer

<400> SEQUENCE: 3
gtgagtcgac atgattagag cctacgaaca aaacc                             35

<210> SEQ ID NO 4
<211> LENGTH: 22
<212> TYPE: DNA
<213> ORGANISM: Artificial Sequence
<220> FEATURE:
<223> OTHER INFORMATION: Yersinia pestis antigen primer

<400> SEQUENCE: 4
tgacgccggc attagagcct ac                                           22

<210> SEQ ID NO 5
<211> LENGTH: 30
<212> TYPE: DNA
<213> ORGANISM: Artificial Sequence
<220> FEATURE:
<223> OTHER INFORMATION: Yersinia pestis antigen primer

<400> SEQUENCE: 5
cgcgaattct catttaccag acgtgtcatc                                   30
```

```
<210> SEQ ID NO 6
<211> LENGTH: 31
<212> TYPE: DNA
<213> ORGANISM: Artificial Sequence
<220> FEATURE:
<223> OTHER INFORMATION: Yersinia pestis antigen primer

<400> SEQUENCE: 6
gcgaattctc aacggttcag tgcttcaata g                                 31
```

COMPOSITIONS, METHODS AND USES FOR EXPRESSION OF ENTEROBACTERIUM-ASSOCIATED PEPTIDES

CROSS-REFERENCE TO RELATED APPLICATIONS

The present application is a national phase application, filed pursuant to 35 U.S.C. 371, that claims the benefit of PCT application No. PCT/US10/58094, filed on Nov. 24, 2010, which claims the benefit of U.S. Provisional Patent Application Ser. No. 61/264,144, filed on Nov. 24, 2009. Pursuant to 35 U.S.C. 119, the prior applications are incorporated herein by reference in their entirety for all purposes.

FEDERALLY FUNDED RESEARCH

Some embodiments disclosed herein were supported in part by grant number 1R43AI061940-01 from the National Institutes of Health. The government may have certain rights in this invention.

FIELD

Embodiments of the present invention report methods, compositions and uses for generating and expressing constructs having enterobacterial-associated peptides. In some embodiments, enterobacterial-associated peptides include, but are not limited to, plague-associated peptides. In certain embodiments, the present invention discloses making and using constructs including, but not limited to, attenuated or modified vaccinia virus vectors expressing enterobacterial-associated peptides.

BACKGROUND

Vaccines to protect against viral infections have been effectively used to reduce the incidence of human disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and generates potent and long-lasting immune responses to the virus. Thus, upon subsequent exposure to a pathogenic strain of the virus, the immunized individual is protected from disease. These live, attenuated viral vaccines are among the most successful vaccines used in public health.

*Yersinia* is a genus of bacteria in the family of Enterobacteriaceae. *Yersinia* are facultative anaerobes. Some members of *Yersinia* are pathogenic in humans. Often, rodents are the natural reservoirs of *Yersinia*; less frequently other mammals may serve as a host to these bacteria. Infection can occur either through arthopod bite, exposure to blood, aerosol transmission (e.g. *Y. pestis*), or by, for example, consumption of food products (e.g. vegetables, milk-derived products and meat) contaminated with the bacteria. Other modes likely exist (e.g. via protozoonitic mechanisms) for transmission. The *Yersinia* family is rather large, but only two have been linked to water-borne outbreaks of disease, *Y. pseudotuberculosis* and *Y. enterocolitica. Yersinia* species are found all over the world in animal reservoirs (e.g., rodent reservoirs for *Y. pestis*), isolated in well-water, water treatment plants, rivers and lakes. *Yersinia pestis* (also referred to as *Pasteurella pestis*) is the most famous member of the *Yersinia* species and is the causative organism of plague.

SUMMARY

Embodiments of the present invention generally relate to methods, compositions and uses for expressing enterobacterial-associated peptides. In some embodiments, enterobacterial-associated peptides include, but are not limited to, plague-associated peptides. Certain embodiments report making and using constructs of the present invention for treating or protecting a subject having been exposed or likely to be exposed to an *Enterobacteria*. In accordance with these embodiments, constructs may include, but are not limited to, attenuated or modified vaccinia virus vectors expressing enterobacterial-associated peptides. In other embodiments, methods and compositions report making and using compositions having constructs including, but not limited to, attenuated or modified vaccinia virus vectors expressing *Yersinia* spp-associated peptides, for example, in order to induce an immune response in a subject against the *Yersinia* spp. Some of these embodiments address a solution for a potential threat of using *Yersinia* spp. as a bioweapon or potential for a *Yersinia* spp. outbreak with its global health implications.

Certain embodiments report composition having constructs with antigens or peptides associated with *Yersinia* spp. including, but not limited to, F1, V, truncated V or YopD polypeptides, or combinations thereof. Other embodiments may include one or more low-calcium response (V) antigens with a C-terminal truncation. In accordance with these embodiments, C-terminal truncation of low-calcium response (V) antigens may include, but are not limited to, a truncation that suppresses expression of a pro-inflammatory cytokine, truncations that remove immunosuppressive sequences, truncations that are less immunosuppressive than corresponding full-length or unmodified LcrV protein, deletion is of up to 163 contiguous residues of LcrV, internal deletions, internal deletion up to 90 contiguous residues, internal deletion extending into the region spanning amino acids 240 to 325 of LcrV protein, C-terminal deletions of up to 50 contiguous residues, an LcrV protein of at least 275 residues in length or combinations thereof. Some embodiments report vaccine compositions capable of reducing or preventing infection in a subject caused by exposure to enterobacteria (e.g. *Yersinia* spp), including, for example, protection from encapsulated and unencapsulated forms of the organism.

In some aspects, constructs of use as vaccine compositions, can include one or more secretory signal sequences alone or in combination with one or more translation control region sequences. In accordance with these embodiments, a secretory signal sequence can be one or more signal sequences functional in mammalian cells. In other embodiments, a secretory signal sequence includes, but is not limited to, tissue plasminogen activator (tPA) leader sequence, the co-factor leader sequence, the pre-proinsulin leader sequence, the invertase leader sequence, the immunoglobulin A leader sequence, the ovalbumin leader sequence, and the P-globin leader sequence or other proleader sequences known in the art.

Vaccine compositions disclosed herein can be administered by any method known in the art. In certain embodiments, a vaccine can be administered intradermally, intramuscularly, by inhalation, intranasally, intravenously or by any other route known in the art. Some compositions can be administered by time-release or other formulations as assessed by a health provider.

Other embodiments concern kits for making or using compositions disclosed. It is reported that a kit may include constructs having a modified vaccinia viral vector and one or more enterobacterial-derived antigen. Other kits can include methods for making a construct contemplated herein.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 5 represents an exemplary assessment of safety of enterobacterial-directed vaccines inoculated in immunocompromised mice.

FIG. 7 represents a compilation of construct data as Table 3.

DEFINITIONS

Figure 1:
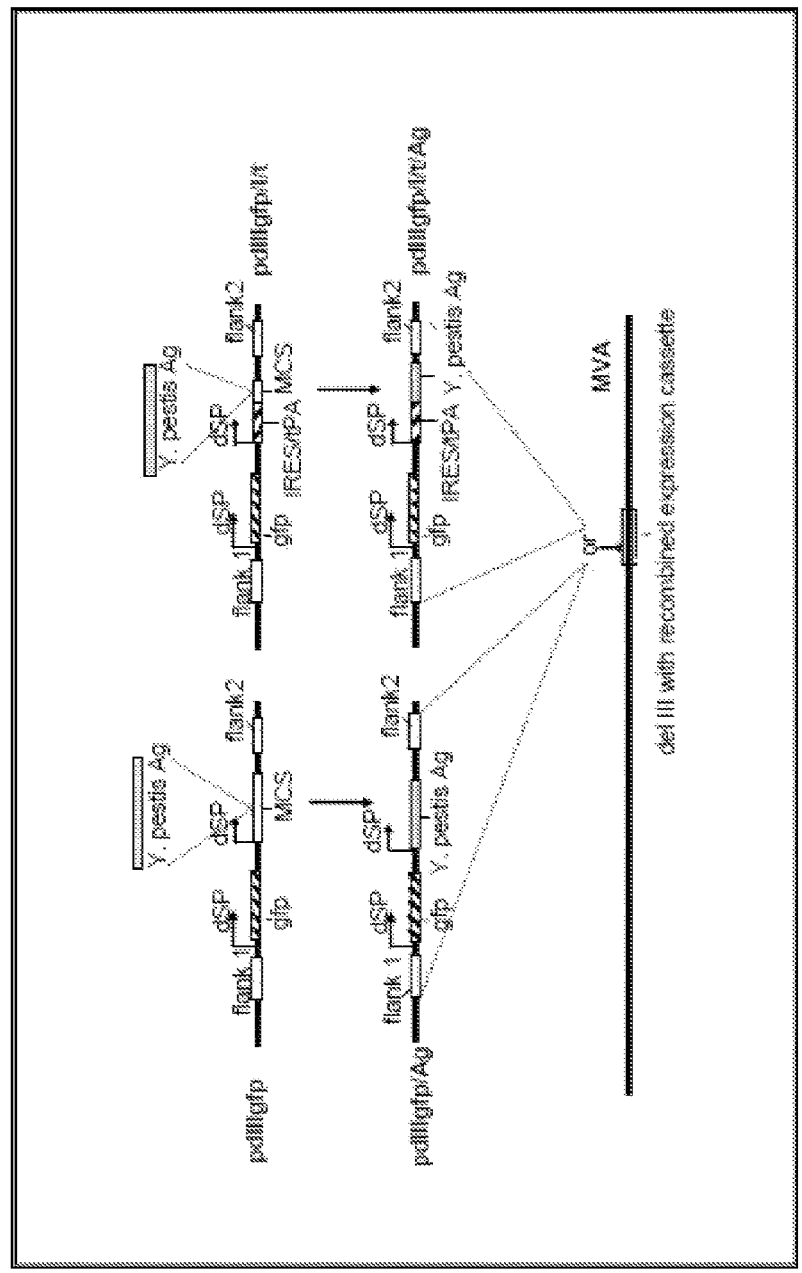
FIG. 1 represents an exemplary construct of modified vaccinia virus and a *Yersinia*-associated peptide.

As used herein, "a" or "an" may mean one or more than one of an item.

As used herein, vessel can include, but is not limited to, test tube, mini- or microfuge tube, channel, vial, microtiter plate or container.

As used herein the specification, "subject" or "subjects" may include, but are not limited to, mammals such as humans or mammals, domesticated or wild, for example dogs, cats, other household pets (e.g. hamster, guinea pig, mouse, rat), ferrets, rabbits, pigs, horses, cattle, prairie dogs, wild rodents, or zoo animals.

As used herein, "about" can mean plus or minus ten percent.

As used herein, "attenuated virus" can mean a virus that demonstrates reduced or no clinical signs of disease when administered to a subject such as a mammal (e.g. human or an animal).

As used herein, "MSC" can mean multiple cloning site.

As used herein, "dSP" can mean divergent vaccinia promoter.

As used herein, "MVA" can mean modified vaccinia Ankara.

As used herein, "EMCV" can mean encephalomyocarditis virus.

As used herein, "IRES" can mean internal ribosome entry site from encephalomyocarditis virus or other viruses.

As used herein, "IRES(A7)" can mean IRES from encephalomyocarditis virus with 7 adenosine residues in bifurcation loop; source-pCITE-1.

As used herein, "IRES(A6)" can mean IRES from encephalomyocarditis virus mutated to have 6 adenosine residues in bifuraction loop.

As used herein, "pDIIIgfp" can mean MVA del III gfp marker transfer plasmid.

As used herein, "pI*" can mean transfer vector plasmids.

As used herein, "tPA" can mean secretory signal from tissue plaminogen activator.

As used herein, "se/l" can mean synthetic optimized early late poxvirus promoter.

As used herein, "H6" can mean the vaccinia gene H6 early/late native poxvirus promoter.

As used herein, "F1" can mean *Y. pestis* capsular protein.

As used herein, "V" can mean *Y. pestis* virulence factor LcrV.

As used herein, "V307" or "$V_{307}$" can mean C-terminal LcrV truncation of amino acids 308-326 of *Y. pestis*. V protein.

As used herein, "YopD" can mean *Y. pestis* outer protein D.

As used herein, "del III" can mean modified vaccinia Ankara deletion region III.

As used herein, "GFP" can mean enhanced green fluorescent protein.

As used herein, "CEF" can mean chicken embryo fibroblasts.

DESCRIPTION

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Some embodiments of the present invention report vaccine compositions including, but not limited to, vaccine compositions having one or more construct comprising modified or attenuated vaccinia virus and one or more enterobacterial-associated peptides. In certain embodiments, a vaccine composition may include a recombinant modified vaccinia Ankara (MVA) vector associated with one or more enterobacterial-associated peptides. In other embodiments, a vaccine composition may include a recombinant modified vaccinia Ankara (MVA) vector associated with one or more enterobacterial-associated peptides where at least one of the enterobacterial-associated peptides includes one or more *Yersinia*-associated peptides. For example, one vaccine composition can include recombinant modified vaccinia Ankara (MVA) vector expressing *Yersinia pestis* antigens. In accordance with this vaccine composition, an MVA construct expressing one or more *Yersinia pestis*-associated antigens may be generated (e.g. V, F1, LcrV protein or mutants or fragments thereof).

Yersinia

Plague is primarily a disease of wild rodents transmitted by fleas, but it can also afflict humans, domestic pets, and wild animals. The disease has devastated human and animal populations throughout history. In recent years, it has caused severe epidemics in many parts of the world, resulting in human deaths and severe economic losses. *Yersinia pestis* is widespread throughout wild rodent populations in the southwestern United States, Southeast Asia, Eastern Europe, central and southern Africa, as well as South America, and human populations in these areas are highly susceptible. In the United States, plague has spread throughout the Western states, causing significant mortality in squirrels, wild mice, and prairie dogs. Domestic cats are also susceptible to *Y. pestis* infections, and they have been identified as the source of infection in many recent cases of plague in humans.

Because of its pathogenicity in humans, particularly the pneumonic form of the disease, and its potential for human-to-human transmission, *Y. pestis* is considered a potential candidate for biowarfare. It is believed that Mongols first used plague as a crude bioweapon in the 1300s during the siege of Kaffa as plague victims were launched over the wall of the city. During World War II, a secret branch of the Japanese army is reported to have dropped plague-infected fleas over China causing several outbreaks in humans. In following years, research programs in biological weapons in the US and Soviet Union successfully developed methods for aerosolization of plague. More recently, evidence that scientists from the former Soviet Union worked with plague serves notice that *Y. pestis* is still considered a feasible bioweapon. In 1970, the World Health Organization estimated that intentional release of 50 kg of the plague bacterium, *Y. pestis*, over a city of 5 million people could result in as many as 150,000 clinical cases and 36,000 deaths. A 2001 U.S. Congressional Office of Technology report estimated that a deliberate aerosol release of *Y. pestis* could cause more than 9,000 clinical cases and at least 2,000 deaths. Therefore, there is an immediate need for novel vaccines that can protect troops, health professionals and first-responder personnel from the threat of *Y. pestis* bioweapons that can limit the spread of disease by vaccination of individuals at risk after a bioterrorist attack and that can limit disease outbreaks in endemic countries.

Certain embodiments of the present invention report compositions having constructs directed against *Yersini* spp. For example, vaccine compositions may be directed to the prevention or reduced incidence of plague.

In recent years the development of novel plague vaccines has been the focus of extensive research, because commercially licensed vaccines based on heat or formaldehyde killed suspension of *Y. pestis*, were found to be unsafe. Capsular F1 (17.5 kDa) and V (35 kDa) antigens are natural virulence factors produced by *Y. pestis*. Both antigens impact innate immune responses required to control bacterial spread at the early stages of infection. F1-based vaccines are immunogenic but these vaccines have failed to provide protection against naturally occurring non-encapsulated strains of *Y. pestis*. Some embodiments of the present invention, may include secreted V antigen which plays for example, a role in delivery of other *Yersinia* outer proteins (Yops) and stimulates secretion of IL-10 (an anti-inflammatory cytokine) associated with the suppression of TNF-α and IFN-γ, a hallmark of plague.

Antigens of use for vaccines against *Yersinia* spp infection may include LcrV (low-calcium-response V or V antigen) or other plasmid-encoded, virulence proteins (e.g. Yops, or *Yersinia* outer proteins) which are essential for survival in mammalian hosts. Yops and LcrV are secreted by a type III mechanism (Ysc), and Yops are unidirectionally targeted into the cytosol of associated eukaryotic cells in a tissue culture infection model. LcrV is required for Yops targeting, and recent findings have revealed that it can localize to the bacterial surface. Therefore, some of the coding sequences of use in some embodiments of the present invention can include coding sequences for *Y. pestis* antigens capsular protein F1, full length virulence factor LcrV (V), a truncated form of LcrV ($V_{307}$), other carboxyterminal truncations of LcrV and effector protein YopD.

Other embodiments may include one or more low-calcium response (V) antigens with a C-terminal truncation. In accordance with these embodiments, C-terminal truncation of low-calcium response (V) antigens may include, but are not limited to, a truncation that suppresses expression of a pro-inflammatory cytokine, truncations that remove immunosuppressive sequences, truncations that are less immunosuppressive that corresponding full-length or unmodified LcrV protein, deletion is of up to 163 contiguous residues of LcrV, internal deletions, internal deletion up to 90 contiguous residues, internal deletion extending into the region spanning amino acids 240 to 325 of LcrV protein, C-terminal deletions of up to 50 contiguous residues, an LcrV protein of at least 275 residues in length (e.g. Schneedind et. al U.S. patent application Ser. No. 11/293,024 filed Dec. 2, 2005, incorporated herein by reference in its entirety for all purposes). In certain embodiments, a modified LcrV protein may suppress expression of a pro-inflammatory cytokine to a lesser extent than a corresponding unmodified LcrV protein. In some embodiments, the pro-inflammatory cytokine may be TNF-α or other known pro-inflammatory cytokines known in the art. In other embodiments, a deletion can include residues 271 to 300 of LcrV protein (rV10). It is contemplated that the same or similar amino acids corresponding to this region of LcrV from *Yersinia pestis* may be deleted in other LcrV proteins. In one example, amino acids 271-300 in *Yersinia pestis* correspond to 280-309 in *Y. enterocolitica*.

In other embodiments, other enterobacteria-derived proteins or peptides can be of use in vaccine constructs contemplated herein for administration to a subject to reduce incidence of or prevent a condition. Certain embodiments report compositions having constructs directed against any pathogenic enterobacterium. For example, vaccine compositions may be directed to the prevention or reduced incidence of an infection in a subject caused by exposure or suspected exposure to a pathogenic enterobacteria. Other enterobacteria can include, but are not limited to *Salmonella* spp., *Shigella* spp, *Escherichia coli* strains or other pathogenic enterobacteria.

Poxviridae

Poxviruses (members of the family Poxviridae) are viruses that can, as a family, infect both vertebrate and invertebrate animals. There are four known genera of poxviruses that may infect humans: orthopox, parapox, yatapox, molluscipox. Orthopox include, but are not limited to, variola virus, vaccinia virus, cowpox virus, monkeypox virus, and smallpox. Parapox include, but are not limited to, orf virus, pseudocowpox, bovine papular stomatitis virus; Yatapox: tanapox virus, yaba monkey tumor virus. Molluscipox include, but are not limited to, molluscum contagiosum virus (MCV). Some of the more common oixviruses are vaccinia and molluscum contagiousum, but monkeypox infections seem to be on the rise.

Poxvirus family, vaccinia virus, has been used to successfully vaccinate against smallpox virus. Vaccinia virus is also used as an effective tool for foreign protein expression to elicit strong host immune response. Vaccinia virus enters cells mainly by cell fusion, although currently the receptor is not known. Virus contains three classes of genes, early, intermediate and late, transcribed by viral RNA polymerase and associated transcription factors. Diseases caused by poxviruses have been known about for centuries.

Orthopoxviruses

Certain embodiments of the present invention may include using modified or attenuated orthopoxviruses in vaccine compositions. Orthopoxvirus is a genus of the Poxviridae family, that includes many agents isolated from mammals, including, but not limited to, vaccinia, monkeypox, cowpox, camelpox, seal poxvirus, buffalo poxvirus, raccoon poxvirus, skunk poxvirus, vole poxvirus and ectromelia viruses. Members of Poxviridae have large linear double-stranded DNA, with genome sizes ranging from 130 to 300 kbp. One of the members of the genus is variola virus, which causes smallpox. Smallpox was previously eradicated using another orthopoxvirus, the vaccinia virus, as a vaccine.

Modified Vaccinia Virus Ankara (MVA)

Some embodiments in the present invention report compositions and methods of use of recombinant vaccinia viruses derived from attenuated poxviruses (e.g., modified vaccinia virus Ankara (MVA), NYVAC, LC16m8 or CVI-78) that are capable of expressing predetermined genes or gene segments. Those skilled in the art recognize that other attenuated poxviruses can be generated by for example, serial passage in cell culture or by deliberate deletion of poxviral genes or other methods known in the art. In certain embodiments, predetermined genes may be inserted at the site of a naturally occurring deletion in the MVA genome. In other embodiments, recombinant MVA viruses can be used, for example, for the production of polypeptides (e.g. antigens) or for encoding antigens of use for vaccine compositions capable of inducing an immune response in a subject administered the vaccine compositions.

In certain embodiments, modified or attenuated poxviruses (e.g. modified vaccinia Ankara (MVA), NYVAC, LC16m8, or CVI-78), can be used in a subject (e.g. mammals such as humans) as a delivery system. Previously, MVA was administered to over 120,000 individuals and proven to be a safe and effective vaccine against small pox. In other embodiments, recombinant MVA vaccine candidates have been shown to induce protective humoral and cellular immunity against diseases caused by viruses, bacteria, parasites, or tumors from which antigens or peptides were derived. Additional features that make MVA a suitable vector include its ability to induce protective immune responses when administered by different routes and its genetic and physical stability properties.

Tranlational Control Sequences

Some embodiments may include an optional enhancer, for example, a translation control sequence. In certain embodiments, a translation control sequence may include an internal ribosomal entry site (IRES) (e.g. EMCV-IRES). Viral IRESs can be classified into four groups: Group 1 (Cricket paralysis virus (CrPV), Plautia stali intestine virus (PSIV) and Taura syndrome virus (TSV)); Group 2 (Hepatitis C virus, (HCV), classical swine fever virus (CSFV) and porcine teschovirus 1 (PTV-1)); Group 3 (encephalomyocarditis virus (EMCV), foot-and-mouth-disease virus (FMDV) and Theiler's Murine Encephalomyelitis virus (TMEV)); and Group 4 (poliovirus (PV) and rhinovirus (RV)). In other embodiments, viral untranslated regions (UTRs) found 5' to viral coding sequences can be used to direct translation. Any translation control sequence of use in viral constructs known in the art is contemplated. In certain embodiments, a viral internal ribosome entry site (IRES) may be used to increase expression of plague antigens contemplated herein. An IRES sequence can be positioned after a stop codon in a messenger RNA molecule and a ribosome can re-attach to the mRNA and a second protein can be translated from the same RNA. Thus, the IRES sequence can be used to express multiple antigens, for instance multiple enterobacterial antigens or an enterobacterial antigen and an antigen from another pathogenic virus or bacterium. For example, if the second protein is a selectable marker, then use of this marker will increase the probability that the gene of interest (placed between the promoter and the IRES) will be expressed by detection of the selectable marker. A number of bicistronic vectors have been produced based on these concepts. Use of any of bicistronic vectors known in the art are contemplated herein.

Secretory Signals

Alternatively, embodiments of the present invention may include constructs having one or more secretory signal sequences. Secretory signals of use can include, but are not limited to, a mammalian secretory signal sequence. Translation control sequences and/or secretory signals were demonstrated to increase efficacy of some vaccines. In some embodiments, one or more secretory signal sequences may include a proleader sequence. In certain examples, a tPA pre-proleader sequence may be used, where a leader sequence includes, but is not limited to, tissue plasminogen activator (tPA) leader sequence, oc-factor leader sequence, pre-proinsulin leader sequence, invertase leader sequence, immunoglobulin A leader sequence, ovalbumin leader sequence, and P-globin leader sequence or other proleader sequences known in the art or a combination thereof.

In some embodiments, designing a construct, such that a protein is expressed, it may be necessary to incorporate into a first nucleic acid region a DNA sequence encoding a signal sequence, for example, in cleavable form, where the expressed protein is desired to be secreted. Without limiting embodiments of the present invention to any one theory or mode of action, a signal sequence can be a peptide that is present on proteins destined either to be secreted or to be membrane bound. These signal sequences are normally located at the N-terminus of the protein and are generally cleaved from the mature protein. The signal sequence generally interacts with the signal recognition particle and directs the ribosome to the endoplasmic reticulum where co-translational insertion takes place. Where the signal sequence is cleavable, it is generally removed by for example, a signal peptidase. The choice of signal sequence which is to be utilized may depend on the requirements of the particular situation and can be determined by the person of skill in the art. In the context of the exemplification provided herein, but without being limited in that regard, tPA may be used to facilitate secretion of a peptide, protein or construct of interest. If a membrane protein is desired, both a 5' cleavable signal sequence at the amino end of the protein and a non-cleavable membrane anchor at the 3' (carboxy) end of the protein may be needed. These could be provided within the vector or one or both could be encoded by the DNA of the protein of interest.

Some embodiments of the present invention include, but are not limited to, compositions including one or more constructs. For example, a construct may be designed to produce proteins or peptides that are cytoplasmically retained, secreted or membrane bound. Deciding what form a protein or peptide of interest may need to take can depend on functional requirements. For example, anchored cell surface expression of a protein of interest provides a convenient means for screening for molecules that interact with the protein of interest such as antibodies, antagonists, agonists or the like particularly to the extent that the protein is expressed on the membrane of an adherent cell type. Still further embodiments concern membrane anchored forms of proteins or peptide that may be suitable for administration to a subject for example, for generating monoclonal antibodies to the protein or peptide. This may be due to host cells providing a source of the protein or peptide that can be correctly folded and have appropriate post-translational modifications, for example, glycosylation and disulphide bond formation. In addition, a host cell may provide adjuvant properties, for example, antigenic differences from a recipient subject, notably in major histocompatibility complexes (MHC).

Alternatively, secreted proteins can be suitable where a protein or peptide is to be harvested and purified. A nucleic acid molecule encoding a signal sequence to the extent that one is utilized, may be positioned in the construct at any suitable location which can be determined as a matter of routine procedure by the person of skill in the art. In some embodiments, a signal sequence may be positioned immediately 5' to the nucleic acid sequence encoding a peptide, protein or construct of interest (such that it can be expressed as an immediately adjacent fusion with the protein of interest) but 3' to a promoter such that expression of a signal sequence is placed under control of the promoter. A nucleic acid sequence encoding a signal sequence can form part of a first nucleic acid region of a construct.

Selection Markers

In certain embodiments, additional selection markers may be used, for example, one may insert any number of selection markers which may be designed, for example, to facilitate the use of the vectors in a variety of ways, such as purification of a molecule of interest. For example, glutathione S-transferase (OST) gene fusion system provides a convenient means of harvesting a construct, protein or peptide of interest. Without limiting to any one theory or mode of action, a GST-fusion protein can be purified, by virtue of the OST tag, using giutathione agarose beads. Embodiments of the present invention should be understood to extend to constructs encoding a secretable GST-molecule fusion. This could be achieved, for example, by designing the sequence of a first nucleic acid region such that it encodes a cleavable signal sequence fused to a cleavable GST which is, in turn, fused to the molecule of interest. In another example, a fusion tag could be used which is itself a fusion between 360 bp of protein A (allowing purification of the secreted product) and beta lactamase (a bacterial enzyme which allows testing of supernatants by a simple colour reaction). Beta lactamase facilitates selection of an assay for a molecule of interest in the absence of an assay for molecule of interest. The protein A/beta lactamase fusion can be separated from the molecule of interest by a cleavage site to facilitate cleavage, so that after the molecule is purified, the tag can be easily removed. Any other selection marker known in the art may be used.

Other fusion tags that could be included to facilitate purification of a molecule or construct of interest include, but are not limited to, staphylococcal protein A, streptococcal protein G, hexahistidine, calmodulin-binding peptides and maltose-binding protein (e.g. the latter is also useful to help ensure correct folding of a molecule of interest). Yet another selectable marker may include an antibiotic resistance gene. Other embodiments may include an antibiotic resistance gene. These genes have previously been utilized in the context of bicistronic vectors as the selection marker or HAT-based selectable bicistronic vector may be used.

Electrophoresis

Electrophoresis ma be used to separate molecules (e.g. large molecules such as proteins or nucleic acids) based on their size and electrical charge. There are many variations of electrophoresis known in the art. A solution through which the molecules move may be free, usually in capillary tubes, or it may be embedded in a matrix. Common matrices include polyacrylamide gels, agarose gels, and filter paper.

Proteins, peptides and/or antibodies or fragments thereof may be purified, partially purified, detected or analyzed by any means known in the art. In certain embodiments, methods for separating and analyzing molecules may be used such as gel electrophoresis or column chromatography methods.

Any method known in the art for detecting, analyzing and/or measuring levels of antibodies may be used in embodiments reported herein. For example, assays for antibodies or antibody fragments may include, but are not limited to, ELISA assays, chemiluminescence assays, flow cytometry and other techniques known in the art.

Imaging Agents and Radioisotopes

In certain embodiments, constructs having proteins or peptides may be linked to a secondary binding ligand or to an enzyme (an enzyme tag) that will generate a fluorescent, a luminescent, or a colored product upon contact with a substrate. Examples of suitable enzymes include luciferase, green fluorescent protein, urease, alkaline phosphatase, (horseradish) hydrogen peroxidase and glucose oxidase. The use and identification of such labels is well known to those of skill in the art.

In other embodiments, labels or molecules capable of detecting peptides, antigens, constructs, antibodies or antibody fragments may include using aptamers. Methods for making and using aptamers are well known in the art and these methods and uses are contemplated herein.

Some embodiments can include methods for detecting and/or making polyclonal or monoclonal antibodies produced by a subject exposed to vaccine compositions disclosed in some embodiments of the present invention. For example, antibodies or antibody fragments produced capable of inducing passive immunity to a subject may be isolated, analyzed and/or produced as a whole antibody or fragment thereof, or a polyclonal or a monoclonal antibody. Any means for producing or analyzing these antibodies known in the art are contemplated.

Nucleic Acid Amplification

Nucleic acid sequences used as a template for amplification can be isolated from viruses, bacteria, cells or cellular components contained in the biological sample, according to standard methodologies. A nucleic acid sequence may be genomic DNA or fractionated or whole cell RNA. Where RNA is used, it may be desired to convert the RNA to a complementary cDNA. In one embodiment, the RNA is whole cell RNA and is used directly as the template for amplification. Any method known in the art for amplifying nucleic acid molecules are contemplated (e.g. PCR, LCR, Qbeta Replicase).

Expressed Proteins or Peptides

Genes or gene segments can be expressed in any number of different recombinant DNA expression systems to generate large amounts of the polypeptide product, which can then be purified and used in methods and compositions reported herein. Any method known in the art for generating and using constructs is contemplated. In certain embodiments, genes or gene fragments encoding one or more polypeptide mays be inserted into an expression vector by standard cloning or subcloning techniques known in the art.

Some embodiments, using a gene or gene fragment encoding a polypeptide may be inserted into an expression vector by standard subcloning techniques. An expression vector may be used which produces the recombinant polypeptide as a fusion protein, allowing rapid affinity purification of a peptide or protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6× His system (Qiagen, Chatsworth, Calif.).

Pharmaceutical Compositions and Routes of Administration

Aqueous compositions of some embodiments herein can include an effective amount of a therapeutic protein, peptide, construct, epitopic core region, stimulator, inhibitor, and the like, dissolved or dispersed in a pharmaceutically acceptable carrier or aqueous medium. Aqueous compositions of vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

Aqueous compositions of some embodiments herein can include an effective amount of a therapeutic protein, peptide, construct, an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds or constructs will then generally be formulated for parenteral administration, e.g., formulated for injection via the intravenous, intramuscular, sub-cutaneous, intralesional, intranasal or even intraperitoneal routes. Any route used for vaccination or boost of a subject can be used. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

If formulations or constructs disclosed herein are used as a therapeutic to boost an immune response in a subject, a therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds or constructs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions can be administered in a manner compatible with the dosage formulation and in such amount as is therapeutically effective. The formulations are easily administered in a variety of dosage forms, such as the type of injectable solutions described above, but slow release capsules or microparticles and microspheres and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion.

The term "unit dose" refers to physically discrete units suitable for use in a subject, each unit containing a predetermined quantity of the construct composition or boost compositions calculated to produce desired responses, discussed above, in association with its administration, e.g., the appropriate route and treatment regimen. The quantity to be administered, both according to number of treatments or vaccinations and unit dose, depends on the subject to be treated, the state of the subject and the protection desired. The person responsible for administration will, in any event, determine the appropriate dose for the individual subject. For example, a subject may be administered a construct composition disclosed herein on a daily or weekly basis for a time period or on a monthly, bi-yearly or yearly basis depending on need or exposure to a pathogenic organism or to a condition in the subject (e.g. cancer).

The active therapeutic agents may be formulated within a mixture to comprise about 0.0001 to 1.0 milligrams, or about 0.001 to 0.1 milligrams, or about 0.1 to 1.0 or even about 10 milligrams per dose or so. Alternatively active agents (e.g. constructs) may be formulated to comprise a certain number of constructs per dose known to produce a desired effect in a subject. Multiple doses can also be administered.

In addition to the compounds formulated for parenteral administration, such as intravenous, intradermal or intramuscular injection, other pharmaceutically acceptable forms include, e.g., tablets or other solids for oral administration; liposomal formulations; time release capsules; biodegradable and any other form currently used.

One may also use intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines and are used for asthma prophylaxis.

Additional formulations which are suitable for other modes of administration can include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Kits

Further embodiments concern kits of use with methods and compositions described herein. Some embodiments concern kits having vaccine compositions of use to prevent or treat subjects having or exposed to an enterobacteria. Kits can be portable, for example, able to be transported and used in remote areas. Other kits may be of use in a health facility to treat a subject having been exposed to an enterobacteria or suspected of being at risk of exposure to an enterobacteria (e.g. *Yersinia* spp).

Other embodiments can concern kits for making and using molecular constructs described herein. In certain embodiments, compositions can include constructs having attenuated or modified MVA and *Yersinia* spp.-associated antigens (e.g. $V_{307}$). Other constructs can also include at least one secretory signal sequence. Yet other embodiments can have a construct that includes translation control sequences (e.g. IRES, UTRs). Other reagents for making and using constructs are contemplated.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the constructs, vaccine compositions and any other reagent containers in close confinement for commercial sale. Such containers may include injection or blow-molded plastic containers into which the desired vials are retained. Optionally, one or more additional agents such as other anti-viral agents, anti-fungal or anti-bacterial agents may be needed for compositions described, for example, for compositions of use as a vaccine.

Dose ranges used during vaccination can vary depending on the nature of the live attenuated vaccine and viral vector used. For recombinant poxviruses these doses can range between $10^5$-$10^7$ PFUs. In certain embodiments of the present invention, immunogenic doses can be as low as $10^2$ pfu. Frequency of vaccination can vary depending on the nature of the vaccine and also the route of administration used. One regimen can include a primary immunization (prime) followed up by a boost administration four to six weeks post-prime immunization. In certain embodiments of the present invention, improvements in antigen translation and expression can permit fewer and/or lower doses to be administered to a subject.

Compositions disclosed herein may be administered by any means known in the art. For example, compositions may include administration to a subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition. Certain compositions can be administered by one route for one boost and another route for a second or additional boost of a composition, as can be pre-determined for a condition or prevention of an infection. In accordance with these embodiments, one boost can be administered intramuscularly and another boost can be administered intradermally or a combinations thereof, depending on a subject's circumstances, as well as dose and frequency determinations for a particular composition.

Preparations

Any method known to one skilled in the art may be used for large scale production of recombinant MVA. For example, master and working seed stocks may be prepared under GMP conditions in qualified primary CEFs or by other methods. Cells may be plated on large surface area flasks, grown to near confluence and infected at selected MOI and vaccine virus purified. Cells may be harvested and intracellular virus released by mechanical disruption, cell debris removed by large-pore depth filtration and host cell DNA digested with endonuclease. Virus particles may be subsequently purified and concentrated by tangential-flow filtration, followed by diafiltration. The resulting concentrated bulk vaccine may be formulated by dilution with a buffer containing stabilizers, filled into vials, and lyophilized. Compositions and formulations may be stored for later use. For use, lyophilized vaccine may be reconstituted by addition of diluent.

Poxviruses are known for their stability. The ability to lyophilize vaccinia for long term, room temperature storage and distribution was one of the key attributes that permitted widespread use of the vaccine and eradication of smallpox. Recently, it was demonstrated that Dryvax vaccinia virus stockpiled in the 60's was still potent after several decades. Procedures for lyophilization and storage of poxviruses are well known in the art and could be applied to the recombinant poxvirus vaccines for some embodiments disclosed herein.

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

EXAMPLES

Example 1

Protein Expression

Figures 2A, 2B, 2C, 2D:
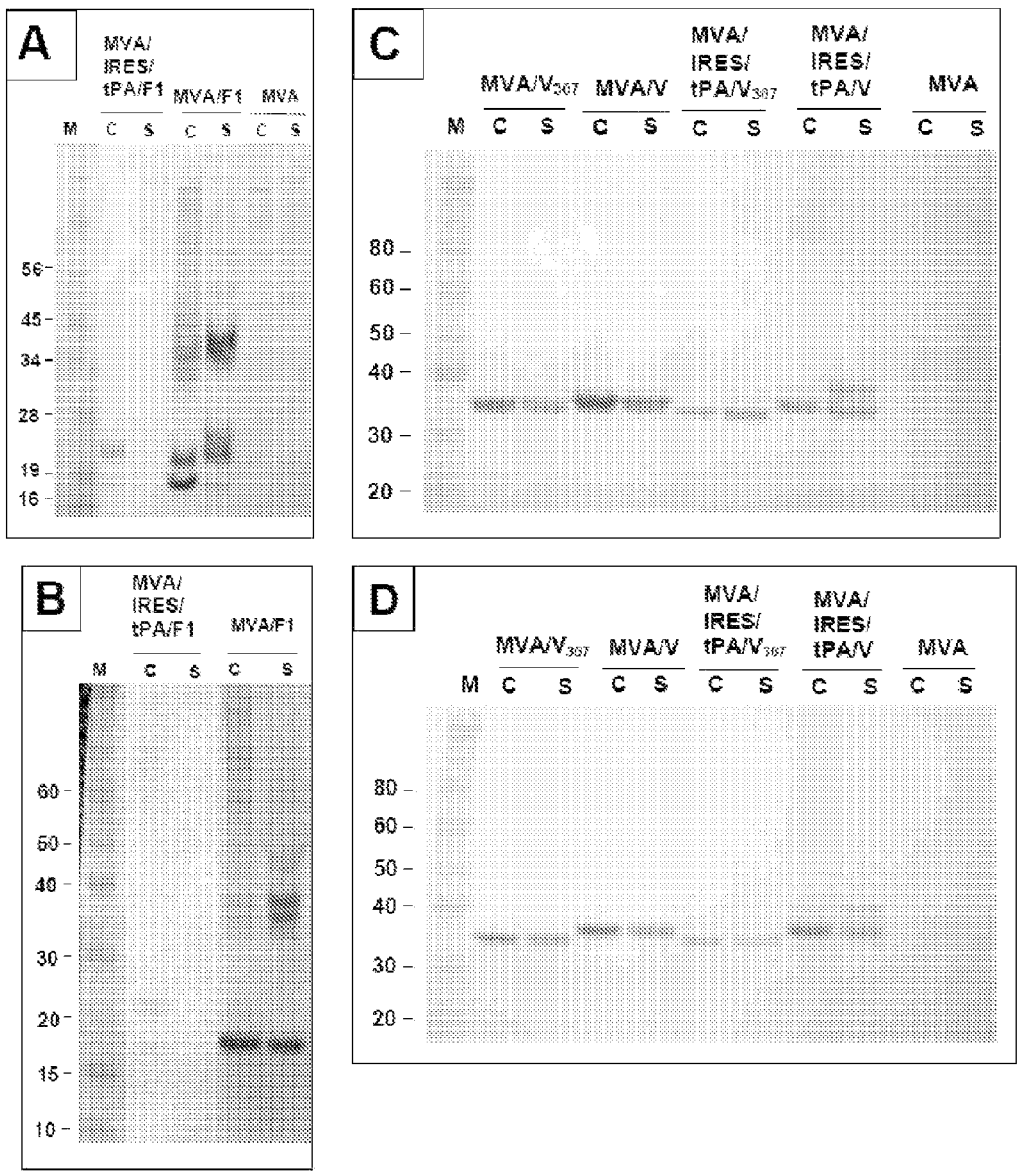
FIGS. 2A-2E represent exemplary electrophoretic separations and analyses of expression patterns from clonal recombinant viruses.
Figure 2E:
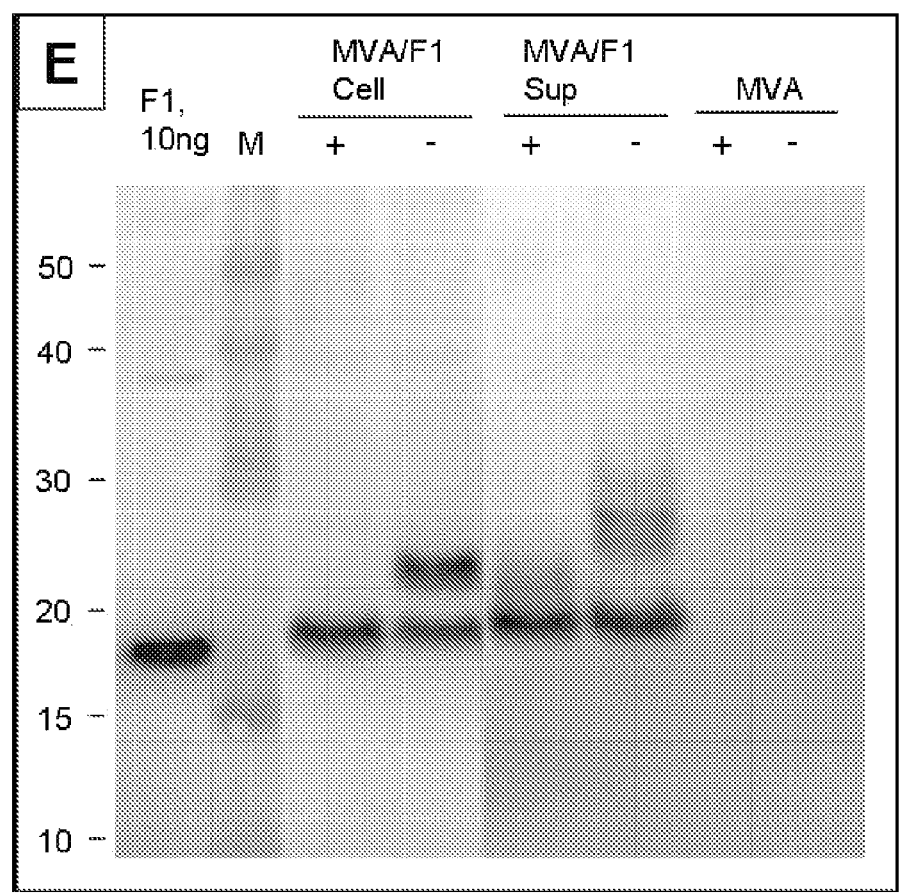

In some exemplary methods, expression of the F1, V and $V_{307}$ antigens of *Y. pestis* was assessed by immuno-blot analyses of proteins from cells infected with the MVA/*Y. pestis* recombinant viruses. Expression levels were evaluated in whole cell extracts and in cell culture supernatants after infection of MVA permissive CEF cells and non-permissive mammalian Vero cells (FIGS. 2A-2E). Expression of the F1 protein by the MVA/F1 recombinant was detected in both the cellular pellet and cell culture supernatants. In MVA/F1 infected CEF cells, the F1 capsular antigen was observed as two lower molecular weight forms consistent with the pre-dicted protein (approximately 18 kilodaltons, kd; predicted protein) and a higher molecular weight form at approximately 23 kd (FIG. 2A). The 23 kd form was more prevalent in the cell supernatant, suggesting that it is preferentially secreted. The capsular F1 protein has one predicted N-glycosylation site and six predicted o-glycosylation sites for vertebrate cells. Thus, it was postulated that the 23 kd form could represent a glycosylated protein. Deglycosylation of CEF-expressed F1 eliminated the 23 kd form and only the 18 kd form remained (FIG. 2E). Higher molecular weight forms of approximately 34 kd and above also were observed in the cell pellets. These forms are consistent with dimers and other multimers; the F1 capsular protein avidly forms multimeric structures upon secretion. These forms were not observed upon extensive denaturation (see for example FIG. 2E). In CEF cells infected with the MVA/IRES/tPA/F1 virus, only low levels of expression of the lower molecular weight forms could be observed in the cell pellets.

In mammalian Vero cells infected with the MVA/F1 recombinant virus, the lower molecular weight form of 18 kd was more predominant than the 23 kd glycosylated form in both the cell pellet and the cell supernatant (FIG. 2B). Again, the 23 kd form disappeared upon deglycosylation (data not shown). Higher molecular weight forms of apparent molecular weights 33, 36 and 39 kd also were detected and were relatively more prominent in the culture supernatants. In Vero cells infected with the MVA/IRES/tPA/F1 recombinant virus, only low levels of expression of the F1 antigen were detected in the cell pellets. The reduced level of expression directed by the IRES/tPA constructs is in contrast to similar constructs made in raccoon poxvirus, previously described. In that case, IRES/tPA directed higher levels of expression and secretion in infected cells.

Expression patterns of V and $V_{307}$ antigens were simpler and were similar in both infected CEF and Vero cells (see for example, FIGS. 2C and 2D). Cells infected with either MVA/V or MVA/$V_{307}$ recombinant viruses expressed a single form of approximately 36 and 35 kd, respectively, consistent with predicted sizes (37 and 35 kd). Cells infected with MVA/IRES/tPA/V expressed two molecular forms of approximately 36 and 40 kd. The higher molecular weight form was consistent with the size of tPA/V fusion and was preferentially secreted. In contrast, cells infected with the MVA/IRES/tPA/$V_{307}$ recombinant virus expressed only a single form of 35 kd. The predicted V and $V_{307}$ open reading frames do not encode consensus glycosylation sequences for vertebrate cells. In the case of V antigen expression, the addition of IRES/tPA slightly reduced protein expression levels. In infected CEF cells, the ratio of secreted to cellular V antigen seemed slightly enhanced with the addition of the IRES/tPA sequence (FIG. 2C). However, the ratios seemed consistent between all the constructs in infected Vero cells (FIG. 2D).

FIGS. 2A-2E illustrates experiments concerning monolayers of CEF or Vero cells transfected with recombinant MVA-plague viruses at MOI of 0.5 pfu/cell. After 48 h post transfection, cells were harvested, cellular and supernatant extracts were prepared and subjected to SDS-PAGE followed by western blot analysis as described in the methods. (A) F1 expression in CEF cellular extracts (c) and supernatant (s) fractions. (B) F1 expression in Vero cell extracts (c) and supernatant (s) fractions. (C) V and $V_{307}$ expression in CEF cell (c) and supernatant (s) fractions. (D) V and $V_{307}$ expression in Vero cell (c) and supernatant (s) fractions. (E) Effect of glycosidase treatment on molecular forms of F1. F1 expression from CEF cell and supernatant (sup) fractions treated with glycosidase (+) or without treatment (−). The F1 control lane contains 10 ng expressed in E. coli from a caf1 operon expression vector (approximate mass 18 kd).

The expression of the F1, V and $V_{307}$ antigens directed by the recombinant MVA viruses was assessed by immuno-blot analyses. Antigen expression from the different MVA recombinants was evaluated in MVA permissive CEF cells and non-permissive mammalian Vero cells (FIGS. 2A and 2B). MVA/F1 recombinants caused expression of F1 proteins of in both cellular extracts and cell supernatants. Due to aggregation of the cF1 capsular antigen, we typically observe both monomer and dimer forms of the F1 protein in SDS-PAGE. Supernatant forms are of higher molecular weight, presumably due to glycosylation of the F1 protein. (FIGS. 2A and B) MVA/V constructs showed significantly higher expression in CEF (FIG. 2C) as compared to Vero (FIG. 2D). MVA/V and MVA/$V_{307}$ had similar expression levels in CEF (FIG. 2C). Although MVA/IRES/tPA/$V_{307}$ expression was lower compared to MVA/V or MVA/$V_{307}$, the V307 protein was more efficiently secreted. (FIG. 2C).

Overview

In one example, a construct composition including a truncated version of the low-calcium response V ($V_{307}$) antigen from Yersinia pestis under translational control of encephalomyocarditis virus (EMVC) internal ribosomal entry site (IRES) and with the tissue plasminogen activator (tPA) secretory signals was administered to mice. The construct composition conferred enhanced immunogenicity and consistently conferred significant protection in mice (87.5%-100%) against intranasal or intraperitoneal challenge with CO92 (encapsulated) or Java 9 (non-encapsulated) strains of Y. pestis, respectively. Although the MVA construct expressing the full version of V antigen was highly immunogenic it provided significantly less protection (37.5%) against CO92 or Java 9 strains, respectively in this experiment. An MVA construct expressing the capsular protein (F1) failed to elicit detectable antibodies but conferred 50% and 25% protection against CO92 or Java 9 challenge, respectively. All the MVA vectored plague vaccines tested in this study were shown to be completely safe in severe combined immuno-deficient (SCID) mice. MVA has been stockpiled for use as a second-generation smallpox vaccine, with superior safety to the original live, attenuated vaccinia strains. Thus, a recombinant MVA/IRES/tPA/$V_{307}$ vaccine has the potential to simultaneously provide protection against smallpox and plague.

In these examples, the following were tested: i) the suitability of MVA to express Y. pestis F1 and V antigens; ii) the immunogenicity and protective capacity of MVA-based recombinants in mice; iii) the influence of an internal ribosomal entry site (IRES) of encephalomyocarditis virus in combination with the secretory signal of tissue plasminogen activator (tPA) on the immunogenicity and protective capacity of MVA-based vaccine candidates; and iv) the safety of MVA recombinants in immunocompromised mice. The findings demonstrated that a recombinant MVA virus expressing a truncated form of Y. pestis V antigen in the presence of the IRES and tPA (MVA/IRES/tPA/$V_{307}$) provided increased immunogenicity, safety, and protection against challenge with different strains of Y. pestis in mice.

In addition, a study of the safety and efficacy of MVA-vectored candidate vaccines that can express and export F1 and V antigens of Y. pestis are described. In immunogenicity studies in BALB/c mice, the MVA-vectored vaccines expressing the V antigen elicited robust antibody responses. Given the strong immunogenic potential of these MVA/V constructs subsequent studies focused on this antigen. The V protein is required for human or animal infectious disease by the three pathogenic Yersinia species, (e.g., Y. enterocolitica, Y. pseudotuberculosis, and Y. pestis). In one example, MVA expressing a variant of the V antigen in which the V antigen is truncated to remove the segment associated with the suppression of endogenous IL-12, TNF-α and IFN-γ in vivo, was tested for immunogenicity and protection. Moreover, effect of combining the IRES translational control sequence with the tPA secretory signal on the immunogenicity and protective capacity of the truncated V antigen was examined. All the MVA constructs expressing the V antigen were found to be immunogenic. When the protective capacities of all generated MVA constructs were tested in a mouse model of pneumonic plague, the MVA/IRES/tPA/$V_{307}$ consistently induced protection against lethal challenge with the highly virulent Y. pestis CO92 strain at 35$LD_{50}$ as well as at 350$LD_{50}$. The protection observed with the MVA/$V_{307}$ construct was significantly lower (P<0.05) than that induced by the MVA/IRES/tPA/$V_{307}$ vaccine. Thus, the IRES/tPA processing signals appear to potentiate the protective immune response In these studies, MVA/F1 vaccine failed to elicit a significant antibody response against the F1 antigen. However, 50% of immunized mice were protected against challenge with Y. pestis CO92 strain with a median survival time of 11 days. Either very low antibody response to F1 or a cellular immune response to the protein may contribute to protect from Y. pestis infection.

Production of high levels of antigen-specific antibodies elicited by the MVA/IRES/tPA/$V_{307}$ construct may account for the high level of protection observed in these studies. However, the MVA/V construct generated high anti-V antibody titers yet less protection from challenge.

Naturally-occurring non-encapsulated variants of Y. pestis have been shown to be virulent. An effective plague vaccine should be able to protect against infection with both encapsulated and non-encapsulated variants of Y. pestis. In these studies, a vaccine candidate construct having MVA/IRES/tPA/$V_{307}$ conferred complete protection against a non-encapsulated strain of Y. pestis (Java 9). Preliminary data suggest that this protection was partially mediated by antibodies; passive transfer of anti-MVA/IRES/tPA/$V_{307}$ antibodies protected from Java 9 challenge.

These MVA vectored plague vaccines were tested for safety in immunocompromised (SCID) mice. Infection of SCID mice with replication competent poxviruses causes significant weight loss and poxvirus lesions analogous to the disseminated viremia that can occur in vaccinated individuals with underlying immune deficiencies. In these studies, it was demonstrated that the MVA constructs expressing plague antigens are safe in SCID mice and fail to induce systemic disease even in the absence of effective B or T cell immunity.

These studies demonstrate the potential of MVA to effectively express Y. pestis antigens and generate protective immune responses. The MVA constructs expressing the V307 antigen in conjunction with signal sequences was shown to be very immunogenic, safe, conferring protection against intranasal or intraperitoneal challenge with Y. pestis.

All the MVA-V constructs were immunogenic, but when tested for protection against plague in mice, the MVA/IRES/tPA/$V_{307}$ induced 87.5 to 100% protection against lethal challenge with the highly virulent Y. pestis CO92 strain. This finding is in agreement with earlier reports indicating improved immunogenic properties of a subunit candidate vaccine based on $V_{307}$ in offering enhanced protection against plague These findings will lead to the development of new vaccination strategies, for example, for biodefense since MVA has been stockpiled for use as a second-generation smallpox vaccine. A vaccine that simultaneously generates protective immune responses to two biological threats, smallpox and plague, may be a valuable biodefense tool.

FIG. 1 illustrates construction of rMVA/Y. pestis antigen viruses. In this example, expression cassettes for each of the Y. pestis antigens, F1, V and $V_{307}$ were inserted into pdIIIGFP. Another cassette contained the EMCV-EMCV IRES sequence followed by the tPA secretory signal was fused to the $V_{307}$ antigen coding sequence. The cassettes were generated by PCR to contain the SmaI and the BamHI restriction sites. Each expression cassette was inserted into a plasmid that contained DNA segments (flank 1 and flank 2) adjacent to deletion III within the HindIII A fragment of MVA. The plasmid also contained a strong synthetic early/late vaccinia virus promoter upstream of a multiple cloning site (MCS) and coding sequences for GFP under the control of a divergent synthetic vaccinia virus early/late promoter.

Example 2

Immunogenicity of MVA Constructs

Figure 3A:
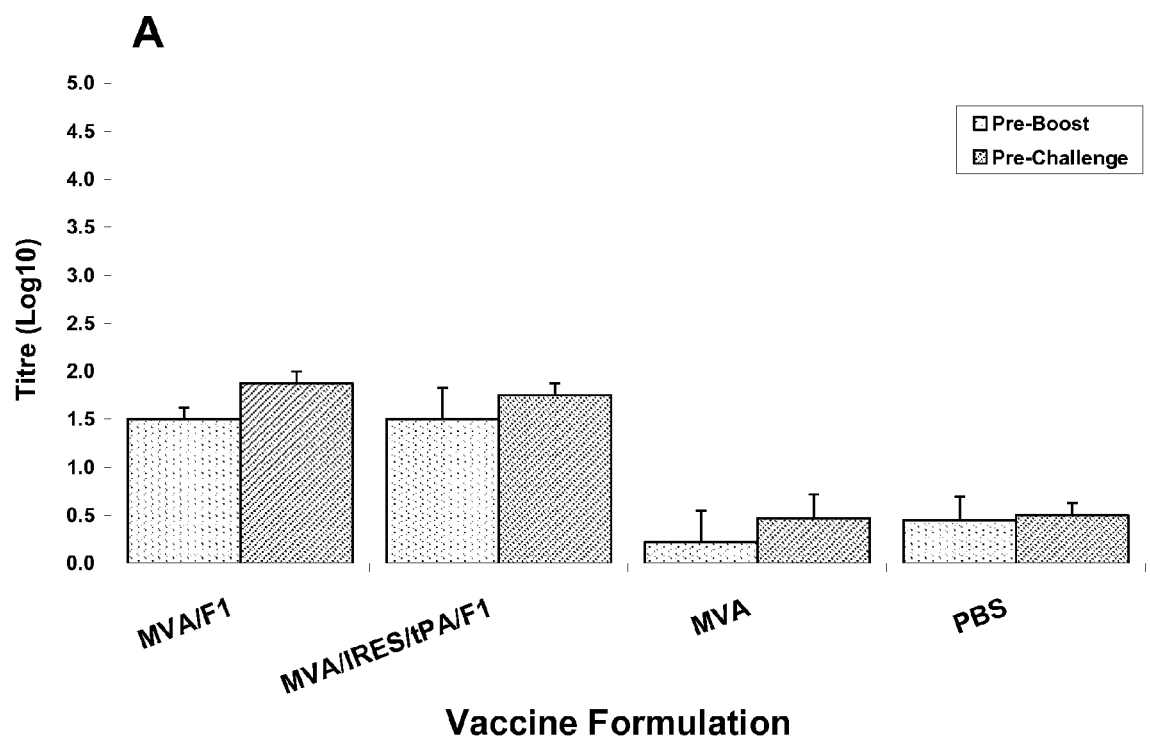
FIG. 3A represents a histogram of an immune response in mice to vaccine of construct compositions of some embodiments disclosed herein, pre-boost and pre-challenge.
Figure 3B:
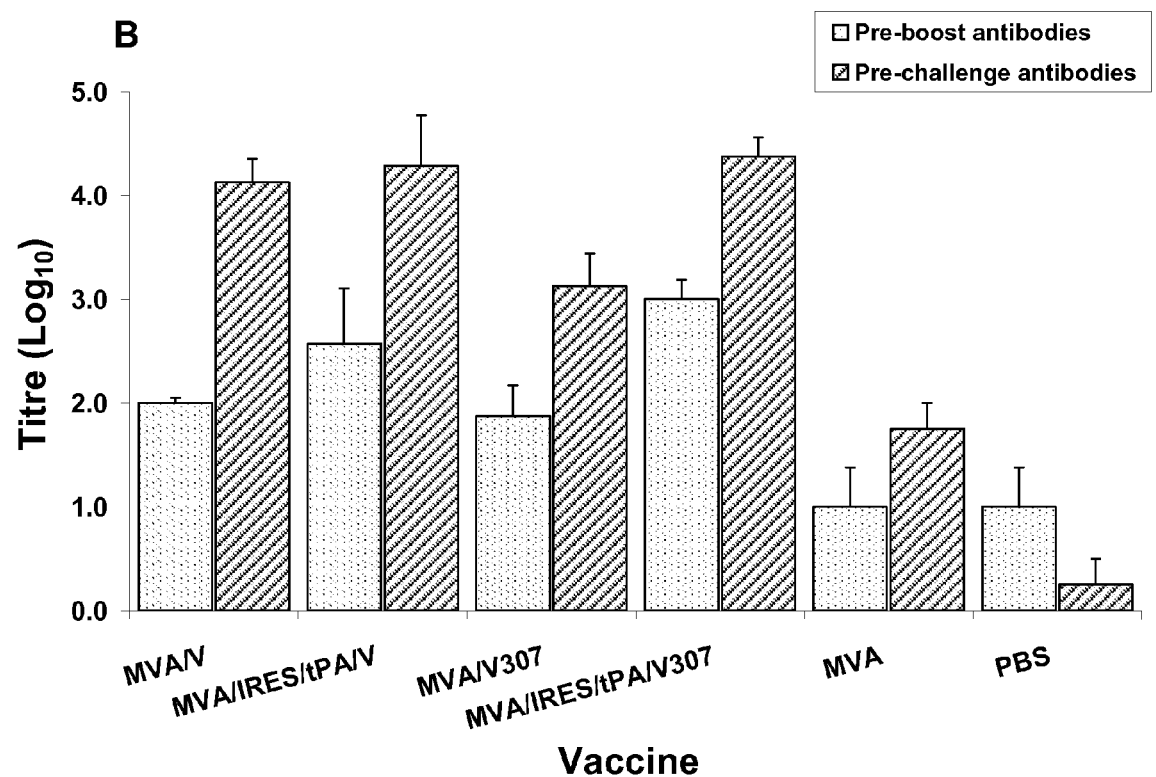
FIG. 3B represents an exemplary histogram of an immune response in mice to vaccine of construct compositions of some embodiments disclosed herein, pre-boost and pre-challenge.

In another exemplary method, groups of BALB/c mice were immunized intramuscularly with MVA/Y. pestis constructs encoding the F1, V or $V_{307}$ antigens. Antibody titers after a single immunization (pre-boost) and after two immunizations (pre-challenge) were assessed by ELISA analysis. Pre-challenge antibody titers elicited by the MVA/V construct were significantly higher (P<0.05) than the MVA/$V_{307}$ construct, however, there was no significant difference between pre-boost titers induced by these constructs (FIG. 3B). The effect of the IRES and tPA sequences on immunogenicity was examined. As shown in FIG. 3B, expression of $V_{307}$ under the control of IRES and secretory signals (MVA/IRES/tPA/$V_{307}$) significantly enhanced its immunogenicity. Both pre-boost and pre-challenge antibody titers were significantly higher (P<0.05) in mice immunized with MVA/IRES/tPA/$V_{307}$ than with MVA/$V_{307}$. Analysis of IgG subclasses elicited by the MVA/IRES/tPA/$V_{307}$ and MVA/$V_{307}$ constructs showed a balanced response between IgG1 and IgG2a subclasses (data not shown). MVA constructs expressing the V antigen induced a significant booster effect (P<0.05) on antibody responses in all immunized mice as compared to primary immunization (FIG. 3B). No booster effect was detected in mice immunized with the MVA/F1 or MVA/IRES/tPA/F1 constructs. Moreover, pre-challenge antibody titers elicited by the MVA/F1 or MVA/IRES/tPA/F1 constructs were significantly lower (P>0.05) than titers induced by constructs expressing the V antigen (FIGS. 3A and 3B).

FIG. 3 illustrates immune responses to MVA/plague vaccines in mice. Groups of eight 4-6 week-old BALB/c mice were vaccinated intramuscularly with MVA-plague vaccines. Following two immunizations separated by 28 days, serum samples collected on days 28 and 42 post-initial vaccinations and analyzed by ELISA to determine humoral immune responses to F1 or V antigens. (A) Antibody responses to F1 antigen. (B) Antibody responses to V antigen from mice immunized with MVA/plague vaccines.

Example 3

Protection Against Plague Challenge

Figure 4A:
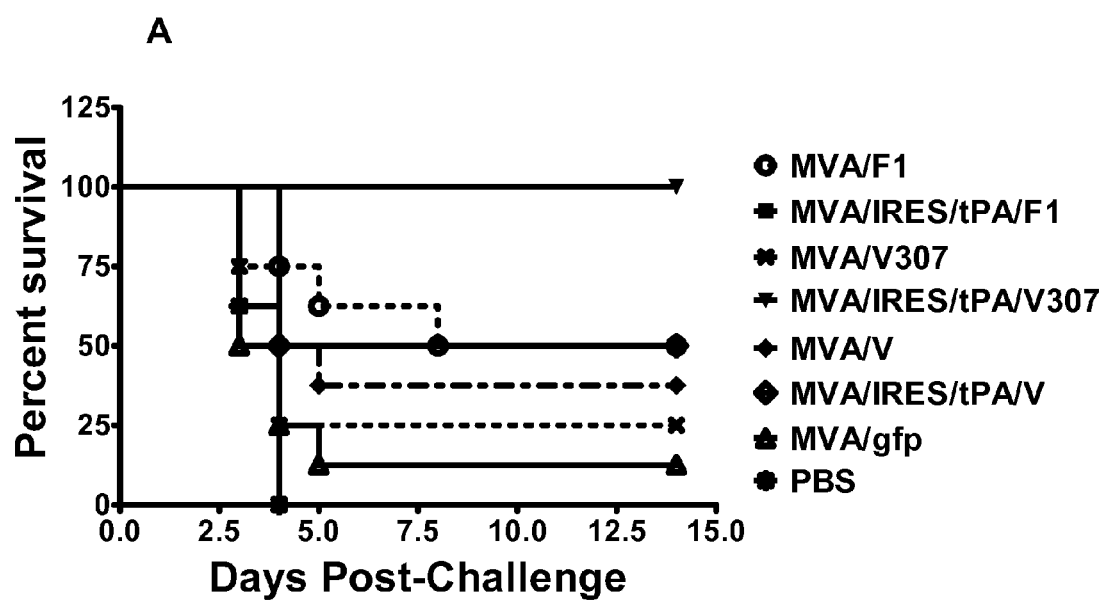
FIG. 4A represents an exemplary plot illustrating survival rates of mice immunized with an exemplary enterobacterial-directed vaccines or control formulations following intranasal challenge with enterobacterium.
Figure 4B:
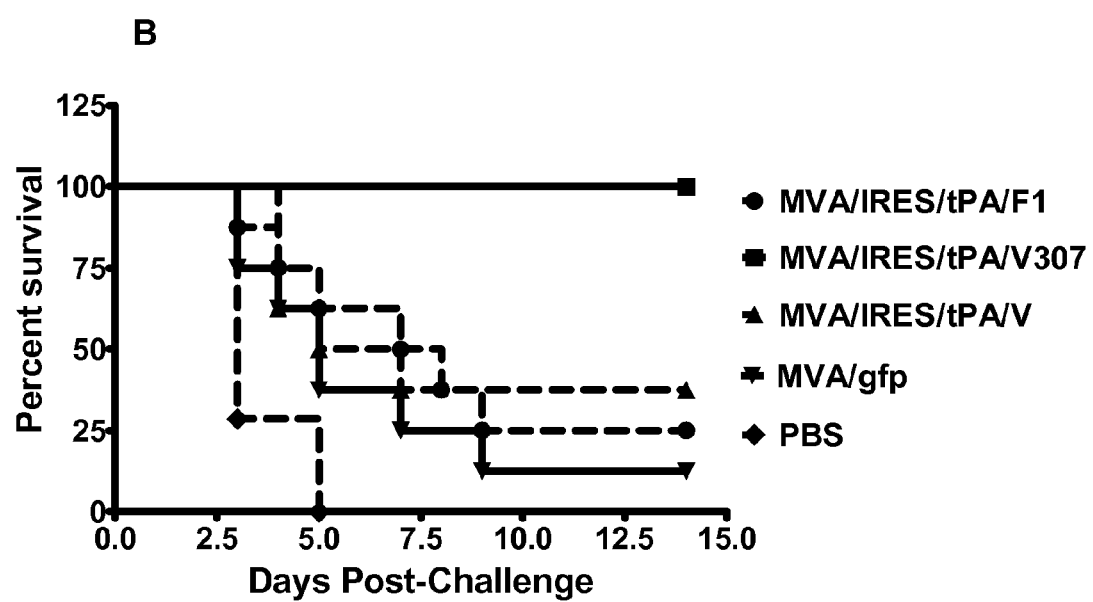
FIG. 4B represents an exemplary plot illustrating survival rates of mice immunized with an exemplary enterobacterial-directed vaccines or control formulations following intraperitoneal challenge with enterobacterium.

In other examples, an animal model was used to assess protection against plague after introduction of some constructs disclosed herein. All mice vaccinated with the MVA/IRES/tPA/$V_{307}$ survived lethal plague challenge with either the CO92 (35 $LD_{50}$) or Java 9 (100 $LD_{50}$) strain of Y. pestis (FIGS. 4A and 4B). Moreover, passive transfer of pooled immune serum from mice immunized with MVA/IRES/tPA/$V_{307}$ to naïve BALB/c mice conferred significant protection (P<0.05) against the Java 9 strain of Y. pestis as compared to the control mice (data not shown). In contrast, only 25%, 37.5% to 50% of mice immunized with MVA/$V_{307}$, MVA/V, or MVA/IRES/tPA/V survived challenge with the CO92 strains of Y. pestis, respectively (FIG. 4A). Mice immunized with MVA/F1 or MVA/IRES/tPA/F1 had 50% or 25% survival rate against challenge with CO92 or Java 9 strain of Y. pestis, respectively (FIGS. 4A and 4B).

FIG. 4 illustrates a Kaplan-Meier survival analysis of mice immunized with MVA/plague vaccines. Two weeks following booster immunizations, mice were challenged (A) intranasally with $1 \times 10^5$ pfu (35$LD_{50}$) of Y. pestis (CO92) or (B) intraperitoneally with 100 cfu (100 $LD_{50}$) of Y. pestis (Java 9) and survival rates were recorded over a period of 2 weeks.

Example 4

Minimal Protective Dose of MVA/IRES/tPA/$V_{307}$ Vaccine

To establish the minimal protective dose of the lead candidate vaccine, groups of 8 BALB/c mice were immunized (prime and boost) with increasing doses ($5 \times 10^5$ pfu, $5 \times 10^6$ pfu or $5 \times 10^7$ pfu) of MVA/IRES/tPA/$V_{307}$ and then challenged with either 35 or 350 $LD_{50}$s of the CO92 Y. pestis strain. Mice immunized with increasing doses of MVA/IRES/tPA/$V_{307}$ elicited corresponding increased immune responses with pre-challenge antibody titers of 3.38, 3.75 or 4.25 (log 10), respectively. The highest immunization dose ($5 \times 10^7$) elicited significantly higher antibody titer (P<0.05) compared to the lower doses and it conferred significant protection (87.5%) against challenge with either 35 or 350 $LD_{50}$s of the CO92 Y. pestis strain, respectively (Table 2, below). There was no significant difference (P>0.05) between survival rates of mice immunized with the two lower doses of the MVA/IRES/tPA/$V_{307}$ vaccine following challenge with 35$LD_{50}$ of Y. pestis (Table 2). A 10-fold increase in the challenge dose (350 $LD_{50}$) reduced the survival conferred by the lowest dose ($5 \times 10^5$ pfu) of the MVA/IRES/tPA/$V_{307}$ vaccine and was not significantly different (P>0.05) from that of the MVA/GFP control group (Table 2). However, significant protection (P=0.01) was conferred on mice immunized with $5 \times 10^6$ pfu of the vaccine against challenge with 350$LD_{50}$ of Y. pestis compared to the control group.

TABLE 2

Survival rate of mice immunized with increasing doses of MVA/IRES/tPA/$V_{307}$ and subsequently challenged via the intranasal route with CO92 strain of Y. pestis

| Vaccination Dose (pfu) | Challenge ($LD_{50}$) | % Survival (14 days post-challenge) | Median Survival Time (Days)[a] |
|---|---|---|---|
| $5 \times 10^5$ | 35 | 62.5 | N/A |
| $5 \times 10^6$ | 35 | 37.5 | 10.5 |
| $5 \times 10^7$ | 35 | 87.5 | N/A |
| $5 \times 10^7$ (MVA) | 35 | 12.5 | 3.0 |
| $5 \times 10^5$ | 350 | 12.5 | 3.0 |
| $5 \times 10^6$ | 350 | 37.5 | 6.0 |
| $5 \times 10^7$ | 350 | 87.5 | N/A |
| $5 \times 10^7$ (MVA/gfp) | 350 | 0.0 | 3.0 |

[a]Median survival time is the time at which 50% of animals have died. This value is not applicable (N/A) for groups with >50% survival rates.

Safety of MVA/Plague Vaccine Candidates in Immunocompromised Mice

Figure 5:
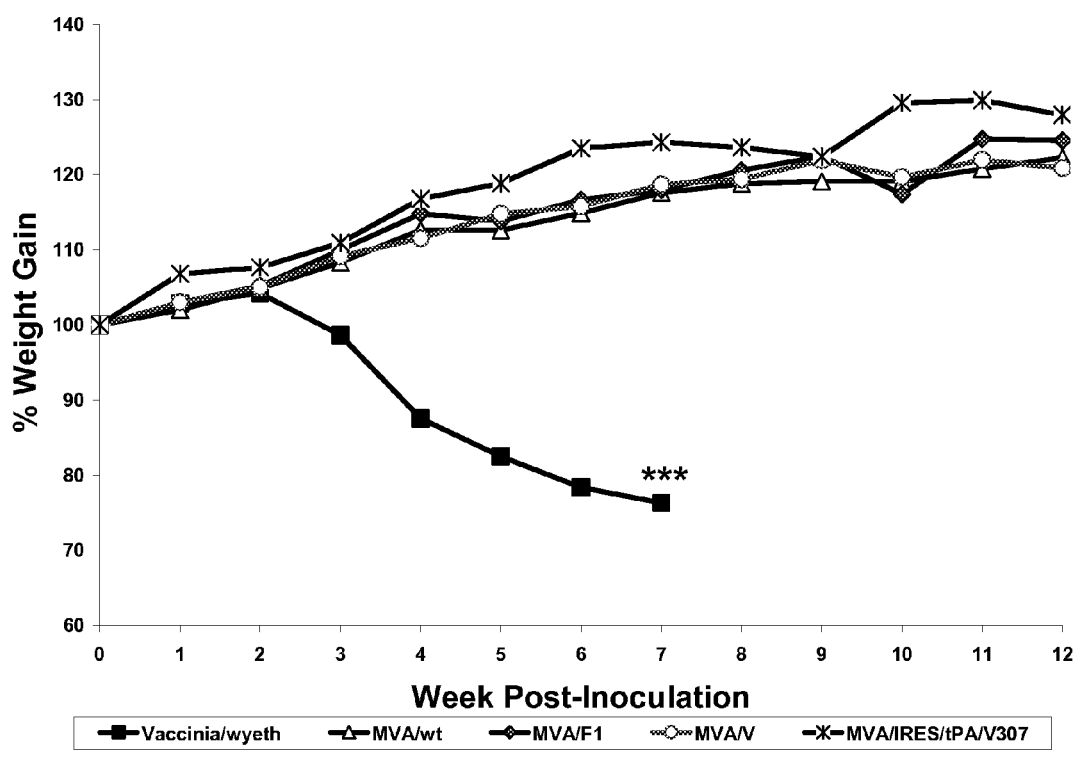

All mice in the vaccinia-Wyeth inoculated-group developed clinical disease symptoms characterized by pox lesions on their tails and feet and persistent weight loss; they died within 5-7 weeks post-infection. None of the animals from the MVAwt or MVA/*Y. pestis* vaccine constructs developed any pox lesions. Weight loss in the vaccinia-Wyeth group was significantly greater (P<0.0001) than in groups that were infected with MVAwt or MVA/plague vaccine constructs (FIG. 5).

Example 5

Antibody Titers

Figure 6:
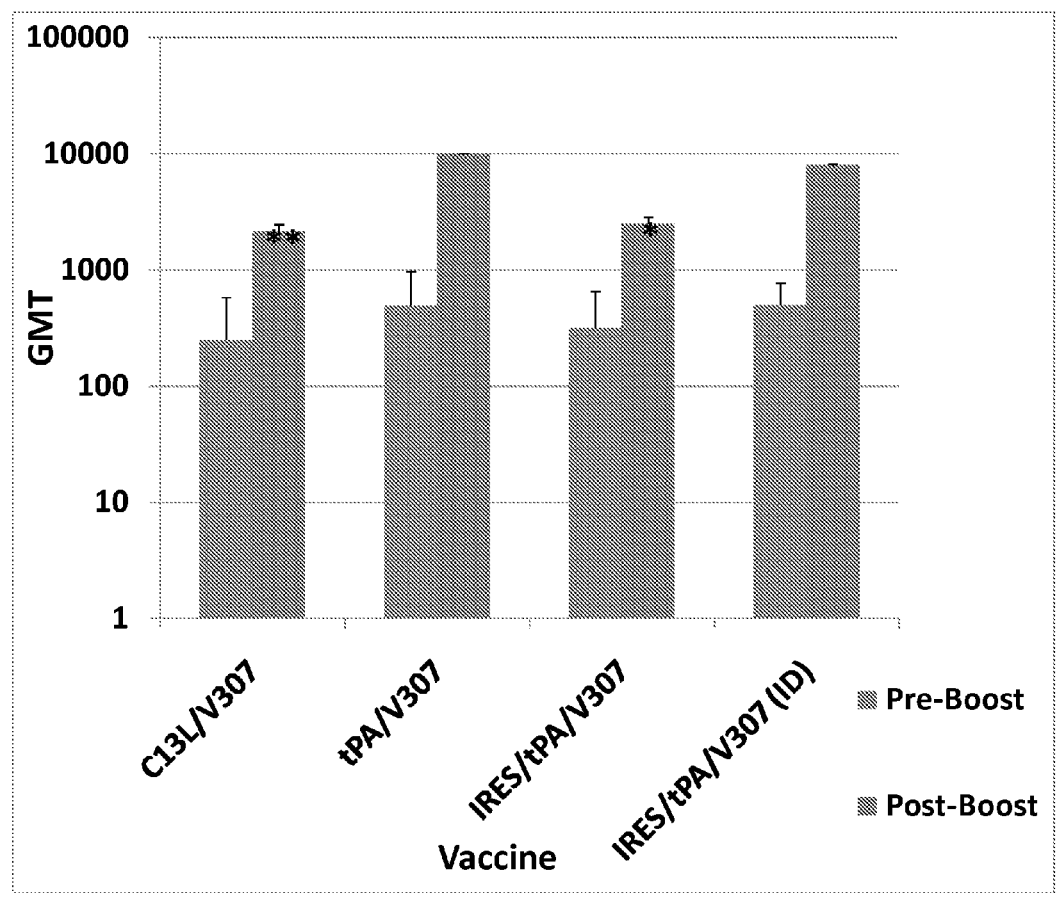
FIG. 6 represents an exemplary plot of antibody titers measured and plotted after IM (intramuscular) or ID (intradermal) pre and post boosts of vaccines of some embodiments disclosed herein.

FIG. 6 represents groups of mice (n=10) were immunized via the intramuscular or intradermal route with $5 \times 10^7$ PFU of MVA/plague vaccines expressing different secretory signals. Antibody titers (Mean±SD) following prime and boost immunization with MVA/Plague vaccines were analyzed by Elisa. Post-boost titers from mice immunized with MVA/tPA/$V_{307}$ (IM) or MVA/IRES/tPA/$V_{307}$ (ID) were significantly higher than MVA/C13L/$V_{307}$ or MVA/IRES/tPA/$V_{307}$ (IM) groups (P values **<0.01, *<0.05).

There were no significant differences between pre-boost antibody titers from the various immunized groups of mice. The co-expression of tPA (MVA/tPA/$V_{307}$) significantly improved the immunogenicity of intramuscularly administered MVA/plague vaccine compared to vaccine co-expressing the C13L secretory signal (MVA/C13L/$V_{307}$, P<0.01) or additionally expressing the IRES translational enhancer (MVA/IRES/tPA/$V_{307}$, P<0.05). Intradermal administration of MVA/IRES/tPA/$V_{307}$ significantly increased (P<0.05) the immunogenicity of the vaccine.

Materials and Methods

Construction of MVA Recombinant Vaccines

The transfer plasmid pdIIIGFP (provided) was used to generate recombinant MVA expressing *Y. pestis* antigens. This plasmid contained: 1) DNA segments (flank 1 and flank 2) adjacent to deletion III within the HindIII A fragment of MVA, 2) a strong synthetic early/late (SEL) vaccinia virus promoter upstream to a multiple cloning site (MCS), and 3) the green fluorescent protein (GFP) gene under the control of a divergent SEL promoter (FIG. 1). A second transfer plasmid, pdIIIGFP/IRES/tPA, containing the ECMV IRES sequence followed by the tPA secretory signal was generated by insertion of an IRES/tPA cassette into pdIIIGFP. Expression cassettes for each of the *Y. pestis* antigens, F1, full lengthV and V truncated at aa 307 ($V_{307}$), were inserted into pdIIIGFP or pdIIIGFP/IRES/tPA. Expression cassettes were generated by PCR (Table 1) to contain appropriate restriction sites for insertion into pdIIIGFP or pdIIIGFP/IRES/tPA. The PCR products were cloned into the MCS of pdIIIGFP or pdIIIGFP/IRES/tPA and the resulting plasmids were designated as pdIIIGFP/F1, pdIIIGFP/IRES/tPA/F1, pdIIIGFP/V, pdIIIGFP/IRES/tPA/V, pdIIIGFP/$V_{307}$ and pdIIIGFP/IRES/tPA/$V_{307}$.

TABLE 1

*Yersinia pestis* antigen PCR primer sequences. Restriction Enzyme sites capitalized.

| | PCR Primer Sequence | RE Site |
|---|---|---|
| 5'F1 | 5'-gtgaGTCGACatgaaaaaaatcagttccgttatc-3' (SEQ. ID. NO: 1) | SalI |
| 3'F1 | 5'-gcGAATTCttattggttagatacggttacggt-3' (SEQ. ID. NO: 2) | EcoRI |
| 5'V native | 5'-gtgaGTCGACatgattagagcctacgaacaaaacc-3' (SEQ. ID. NO: 3) | SalI |
| 5'V I/t | 5'-tgacGCCGGCattagagcctac-3' (SEQ. ID. NO: 4) | NgoMIV |
| 3'V full | 5'-cgcGAATTCtcatttaccagacgtgtcatc-3' (SEQ. ID. NO: 5) | EcoRI |
| 3'$V_{307}$ | 5'-gcGAATTCtcaacggttcagtgcttcaatag-3' (SEQ. ID. NO: 6) | EcoRI |

Recombinant MVA-plague viruses were generated as described previously. Briefly, chicken embryo fibroblasts (CEF), were infected with wild type MVA at a multiplicity of 0.05 and one hour (h) later the cells were transfected with each of the transfer vectors using Lipofectamine™ (Invitrogen, Carlsbad, Calif.). At 48-72 h post-transfection, monolayers were harvested, centrifuged at 500 RCF for 5 minutes at 4° C. and cells disrupted by freeze-thaw and sonication (2 times for 15 seconds using a Virtis600 at setting 3). The disrupted cell extracts containing possible recombinant viruses expressing GFP were plated onto fresh CEF cells and overlaid with 0.8% agarose. After 48-72 h, recombinant virus-generated plaques were detected by fluorescence and picked into media with a glass pipette. The cell/virus samples were sonicated and plated as described above. After three consecutive rounds of plaque isolation, high titer virus stocks were prepared in CEF cells for subsequent in vitro and in vivo characterization.

In Vitro Expression of *Y. pestis* Antigens

The in vitro expression of recombinant MVA viruses containing the F1, V, $V_{307}$ or IRES/tPA/F1, IRES/tPA/V, IRES/ tPA/$V_{307}$ antigens was determined by immuno-blot analyses. CEF or Vero cells were plated into 6-well plates and infected with the recombinant MVA/F1, MVA/IRES/tPA/F1, MVA/V, MVA/IRES/tPA/V, MVA/$V_{307}$ or MVA/IRES/tPA/$V_{307}$ viruses at an MOI of 0.5 or 5, respectively in serum free conditions. At 48 h post-infection, the infected cells were harvested in the presence of a protease inhibitor cocktail (Mini Protease tabs, Roche Diagnostics, Indianapolis, Ind.), washed, resuspended in 1× loading buffer and heated to 95° C. for 5 min. The supernatants from the infected cells were centrifuged and concentrated by ultrafiltration with a 3 kDa cutoff membrane (Nanosep 3K Omega, Pall, Inc., East Hills, N.Y.). The supernatants were then combined with an equal volume of 2× loading buffer and heated to 95° C. for 5 min. Supernatant and cell samples were resolved by SDS polyacrylamide gel electrophoresis (SDS-PAGE) and transferred to a nitrocellulose membrane for immuno-blot analysis using polyclonal rabbit anti-F1 or anti-V serum produced in-house. The polyclonal antibodies were generated by inoculating specific pathogen free (SPF) rabbits with purified F1 (from caf1 operon expression system) or V (ATCC, BEI Resources, Manassas, Va., cat# NR-3832) proteins. These antibodies showed minor background to MVA wild type expressed from CEF or Vero when used in immunoblot analyses.

The F1 glycosylation state was analyzed using a protein deglycosylation enzyme mix (New England Biolabs (NEB), Ipswich, Mass., cat# P6039S). Briefly, Vero and CEF cells were infected with MVA/F1 or MVA/IRES/tPA/F1 and harvested as previously described. The cell pellets, suspended in 30 ul $H_2O$, and concentrated supernatants were processed using the NEB kit protocol. 18 μl of the resuspended cell pellet and concentrated supernatant samples, were denatured for 10 minutes at 100° C. G7 reaction buffer containing 10% NP40 was added to bring the reaction volume to 50 μl. Each reaction was split and half was treated with 2.5 ul NEB deglycosylation enzyme cocktail and incubated at 37° C. for 4 hr. 10 ul, of each reaction, was subjected to electrophoresis and analyzed by Western using the polyclonal rabbit anti-F1 serum.

*Yersinia pestis* Cultures

Preparation of *Y. pestis* cultures and subsequent animal challenge experiments were conducted as previously described. Briefly, to prepare a working stock, 75 μL of the frozen *Y. pestis* isolate was thawed, vortexed, spread onto blood agar plates (Remel, Lenexa, Kans.), and incubated at 28° C. for 48 h. The bacterial lawn was scraped from the agar plates into 200 ml Heart Infusion Broth (Difco Laboratories, Detroit, Mich.) with 0.2% xylose and incubated at 28° C. for 48 h. Final stocks were prepared by adding 20% glycerol to the broth culture (v/v) and were stored in aliquots at −80° C. The bacterial strains CO92 and Java 9 of *Y. pestis* were provided. The F⁻ strain of choice for these studies would have been the C12 strain (this one was not available at the time); so F1⁻ Java 9 which was readily available was used.

Immunization and Challenge

Groups of eight 4-6 week-old female BALB/c mice (Harlan Sprague Dawley, Indianapolis, Ind.) received primary and booster immunizations (28 days apart) with each vaccine candidate via intramuscular injections into the hind legs. A dose of $5\times10^7$ plaque forming units (pfu) in 50 μl was used for both injections. Control groups were immunized with either recombinant F1 protein (rF1—40 μg), empty MVA vector (MVA/GFP—$5\times10^7$ pfu) or with phosphate buffered saline (PBS—50 μL). At two weeks post-boost, all animals were challenged with the wild-type *Y. pestis* CO92 strain by intranasal instillation of 10 μL (5 μL into each nostril) of inoculum containing $1\times10^5$ colony forming units (cfu) ($35LD_{50}$) of the bacteria. Animals challenged with the Java 9 strain of *Y. pestis* received 100 μl inoculum containing 100 cfu ($100LD_{50}$) intraperitoneally. The isolate of Java 9 used in this study was less virulent via the intranasal route but highly virulent when used intraperitoneally. Challenged animals were monitored for two weeks.

A group of eight 4-6 week-old naïve mice was passively immunized intraperitoneally with 100 μl of post-boost pooled serum with a titer of 100,000 from mice immunized with two doses of MVA/IRES/tPA/$V_{307}$. The passively immunized mice were challenged intraperitoneally with a 100 μl inoculum containing 100 cfu ($100LD_{50}$) of the Java 9 strain of *Y. pestis*. Challenged animals were monitored for two weeks. The stability and virulent phenotype of the *Y. pestis* CO92 or Java 9 frozen stock cultures were validated by testing aliquots for bacterial counts and lethal doses. The number of colony-forming units was determined by plating 100 μL of each dilution onto blood agar and incubating at 28° C. for 48 h. Lethal dose ($LD_{50}$) values were determined by inoculating groups of 11-12 week-old BALB/c mice intranasally (10 μL) or intraperitoneally (100 μL) with 10-fold dilutions of the *Y. pestis* CO92 or Java 9 bacterial cultures, respectively. Following inoculation, animals were monitored for 14 days, mortalities were recorded and $LD_{50}$ was calculated by a method known in the art.

Serology

Serum samples were collected on day 28 post-primary vaccination and day 14 post-boost (pre-challenge) to assess antibody titers against *Y. pestis* F1 or V antigens. Serum total IgG as well as IgG1 and IgG2a subclass titers were measured by enzyme-linked immunosorbent assay (ELISA) as described previously. Briefly, 96-well ELISA plates were coated with purified recombinant F1 or V antigen (0.1 μg in 100 μL carbonate buffer, pH 9.6 per well) at 4° C. overnight. Coated plates were washed twice with 0.05% TWEEN 20 in PBS (washing buffer) and rinsed with blocking buffer (1% BSA in PBS) for 1 h at room temperature (RT). Serum samples then were serially diluted from 1:100-1:100,000 in ELISA diluent (0.1% BSA in washing buffer) and added in triplicate to the prepared ELISA plates. Known negative and positive serum samples from mice inoculated with recombinant F1 or V antigen from previous studies were used as controls and plates were incubated for 1 h at RT. After washing, 100 μL per well of a 1:10,000 dilution of horseradish peroxidase (HRP)-conjugated rabbit anti-mouse IgG (Abcam Inc, Cambridge, Mass.) was added to each well and incubated for 1 h at RT. Plates were washed, and 100 μL per well of tetra-methyl-benzidine (TMB) chromogen (Invitrogen, Calsbad, Calif.) was added to each well and incubated in the dark for 5 minutes. The reaction was then stopped by adding 100 μL per well of 2 mM $H_2SO_4$ (Sigma, St Louis, Mo.). Colorimetry was assessed using a microplate reader (ELx800-BioTek, Winooski, Vt.) at test wavelength of 450 nm and a reference wavelength of 630 nm. The highest dilution that was positive (exceeded the mean of known negative serum samples plus three standard deviations) was considered the endpoint, and its reciprocal value was recorded as the titer.

Groups of six, five-week old BALB/c SCID mice (Harlan Sprague Dawley, Indianapolis, Ind.) were inoculated intraperitoneally with $1\times10^8$ pfu of MVA/F1, MVA/V, MVA/$V_{307}$, MVA/IRES/tPA/$V_{307}$ or wild type MVA (MVAwt). An additional group received $1\times10^6$ pfu of the vaccinia Wyeth strain via the same route. Mice were monitored daily for 3 months and their weight was recorded weekly. Mice died naturally or were euthanized when showing body-conditioning score less than two (BCS<2) as previously described.

Statistical Analysis

One way ANOVA was used to evaluate the vaccine group effects on pre-boost and pre-challenge antibody titers. If the vaccine group effect was statistically significant ($P<0.05$ by Kruskal-Wallis test), an all pair-wise comparison among groups was performed using an unadjusted P-value of 0.05. Survival analysis was performed to assess vaccine effectiveness against challenge with either CO92 or Java 9; reported P-values are from Fisher's exact test. Probability values<0.05 were considered significant using the GraphPad Prism 5 software (La Jolla, Calif.) for all statistical analyses.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

---

What is claimed is:

1. An immunogenic composition comprising:
   one or more constructs of live attenuated, modified vaccinia Ankara (MVA) viruses encoding:
   at least one $V_{307}$ peptide which is the C-terminally truncated low-calcium response V (LcrV) protein antigen of Yersinia pestis lacking its C-terminal amino acids 308 to 326 and
   a mammalian secretory signal sequence and a viral translational control sequence, wherein the mammalian secretory signal sequence is tissue plasminogen activator (tPA) secretory signal and the viral translational control sequence is a viral internal ribosomal entry site (IRES), wherein the one or more constructs in the composition are capable of inducing a protective immune response to one more strains of Yersinia pestis in a mammalian subject.

2. The composition of claim 1, wherein the protective immune response induced is against encapsulated and non-encapsulated strains of Yersinia pestis.

3. The composition of claim 1, wherein the viral IRES is from encephalomyocarditis virus (EMCV).

4. The composition of claim 1, wherein the at least one $V_{307}$ peptide lacks immunosuppressive sequences of the LcrV protein antigen.

5. The composition of claim 1, wherein the composition comprises a pharmaceutically acceptable carrier.

6. A kit comprising the composition of claim 1 and at least one container.

7. The kit of claim 6, further comprising a delivery device for delivery to the subject.

8. A method of inducing a protective immune response in a mammalian subject comprising administering the composition of claim 1 to the subject.

9. An immunogenic composition for administration to a mammalian subject comprising a pharmaceutically acceptable carrier and
   one or more constructs of live attenuated, modified vaccinia Ankara (MVA) viruses encoding:
   at least one $V_{307}$ peptide which is the C-terminally truncated low-calcium response V (LcrV) protein antigen of Yersinia pestis lacking its C-terminal amino acids 308 to 326 and
   a mammalian secretory signal sequence and a viral translational control sequence, wherein the mammalian secretory signal sequence is tissue plasminogen activator (tPA) secretory signal and the viral translational control sequence is encephalomyocarditis virus (EMCV) internal ribosomal entry site (IRES), wherein the one or more constructs in the composition are capable of inducing a protective immune response to one more strains of Yersinia pestis in the subject.

* * * * *

UNITED STATES PATENT AND TRADEMARK OFFICE
CERTIFICATE OF CORRECTION

Page 1 of 1

PATENT NO. : 9,028,809 B2
APPLICATION NO. : 13/511652
DATED : May 12, 2015
INVENTOR(S) : Dan T. Stinchcomb et al.

It is certified that error appears in the above-identified patent and that said Letters Patent is hereby corrected as shown below:

In the Specification:

Column 1, lines approximately 20-23,

Replace paragraph [0002] of the application as filed under FEDERALLY FUNDED RESEARCH with the corrected paragraph below:

"This invention was made with Government support under R43 AI061940 awarded by the National Institutes of Health. The Government has certain rights in this invention."

Signed and Sealed this
Eighteenth Day of August, 2015

Michelle K. Lee
*Director of the United States Patent and Trademark Office*